(12) United States Patent
Bainczyk et al.

(10) Patent No.: US 8,777,872 B2
(45) Date of Patent: Jul. 15, 2014

(54) DIAGNOSTIC SYSTEM FOR DETERMINING SUBSTANCE CONCENTRATIONS IN LIQUID SAMPLES

(75) Inventors: Grogor Bainczyk, Mannheim (DE); Michael Marquant, Mannehim (DE); Herbert Wieder, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 946 days.

(21) Appl. No.: 11/754,803

(22) Filed: May 29, 2007

(65) Prior Publication Data
US 2007/0293790 A1    Dec. 20, 2007

Related U.S. Application Data

(63) Continuation of application No. PCT/EP2005/012568, filed on Nov. 24, 2005.

(30) Foreign Application Priority Data

Nov. 29, 2004    (DE) .......................... 10 2004 057 503

(51) Int. Cl.
*A61B 5/00*    (2006.01)

(52) U.S. Cl.
USPC ........................................................ 600/583

(58) Field of Classification Search
USPC ......... 600/300, 573, 576, 577, 578, 579, 580, 600/583, 584; 604/4.01, 6.15, 6.16
See application file for complete search history.

(56) References Cited

U.S. PATENT DOCUMENTS

| | | | |
|---|---|---|---|
| 6,302,855 B1 | 10/2001 | Lav et al. |
| 6,379,317 B1 | 4/2002 | Kintzig et al. |
| 6,419,661 B1 | 7/2002 | Kuhr et al. |
| 6,540,672 B1 | 4/2003 | Simonsen et al. |

FOREIGN PATENT DOCUMENTS

| | | |
|---|---|---|
| EP | 1048310 B1 | 11/2000 |
| EP | 1321769 B1 | 6/2003 |
| JP | 2001-524680 A | 12/2001 |
| WO | 02/55008 A2 | 7/2002 |
| WO | 03/082091 A2 | 10/2003 |
| WO | 03/083469 A2 | 10/2003 |
| WO | 2004/078233 A2 | 9/2004 |

*Primary Examiner* — Max Hindenburg
(74) *Attorney, Agent, or Firm* — Roche Diagnostics Operations, Inc.

(57) ABSTRACT

A diagnostic system has a diagnostic module with an integrated lancet system and a magazine module separate from the diagnostic module. The diagnostic device also has a connecting device that is used for tensioning the lancet system.

36 Claims, 7 Drawing Sheets

DIAGNOSTIC SYSTEM FOR DETERMINING SUBSTANCE CONCENTRATIONS IN LIQUID SAMPLES

REFERENCE TO RELATED APPLICATIONS

The present application is a Continuation of PCT Patent Application No. PCT/EP2005/012568, filed Nov. 24, 2005 which claims priority to German Patent Application No. DE 10 2004 057 503.7, filed Nov. 29, 2004, which are hereby incorporated by reference in their entirety.

TECHNICAL FIELD

The invention relates to a diagnostic system for determining substance concentrations in liquid samples, particularly for measuring blood glucose concentration. The invention further relates to a method for operating a diagnostic system according to the invention.

BACKGROUND

Monitoring of blood glucose concentration is, for diabetics, an essential part of their daily routine. The blood glucose concentration has to be determined quickly and easily, and several times a day, to determine suitable medical steps. To ensure that the diabetic's daily routine is impinged on no more than is necessary, suitable portable appliances are often used so that the blood glucose can be measured at the workplace during leisure time.

Various portable appliances are presently available on the market, some of them functioning according to different measurement methods. For example optical or electro-chemical measurement methods are used in such diagnostic devices. One example of a frequently employed measurement method uses a special kind of electrochemical test strips. These test strips are designed in such a way that a predefined amount of blood is guided via a capillary system to an electrode system. For modem test strips, a blood quantity of ca. 1.5 microliters is sufficient, in some cases even quantities of blood of less than one miroliter. The electrode system can, for example, involve gold electrodes which are provided with a coating. The coating in most cases contains various enzymes and so-called mediators and has the effect that charge carriers (for example in the form of redox molecules) form within the sample on the electrodes, the concentration of these charge carriers being dependent on the blood glucose concentration. The concentration of these charge carriers can be determined by means of the gold electrodes and a suitable measurement system known to the skilled person, for example by means of a comparatively simple current-voltage measurement, and thus calculated back to the blood glucose concentration.

An important element of portable diagnostic systems of this kind is thus represented by the corresponding test strips and by the systems for output of these test strips. About 5 to 7 such test strips are typically needed each day by a diabetic. It is imperative that the test strips are kept clean and dry in order to ensure that the measurement of the blood glucose concentration is not rendered false by corresponding soiling or by the action of moisture.

Prior art systems are known with means for storing and outputting of test strips. The device described essentially comprises an arrangement which is moisture-tight and airtight and in which corresponding test strips are stored and can be output by means of a slide device. However, prior art devices do not contain any means for diagnosis, i.e. for measuring the blood glucose concentration for example. Moreover, the described device does not include any means for preparing suitable samples, for example a lancet system for obtaining drops of blood. Therefore, the device described in EP 1 321 769 A1 can be used only in combination with suitable lancet systems and diagnostic systems for evaluation of the test strips.

A device for storing and outputting of test strips is also disclosed in WO 02/055008 A2. In the latter, a test strip cassette is stored in a tube which is in turn accommodated in a housing. The housing has a button and mechanism by means of which a test strip can be output from the tube. WO 02/055008 too does not describe a complete diagnostic system, but only a suitable output unit for test strips, which unit can be used only in combination with other systems, in particular with a lancet system and a diagnostic or measurement system. This greatly increases the space taken up by the devices required for routine monitoring of blood glucose concentrations.

WO 03/083469 A2 discloses an integrated test appliance which, for example, can be used for electrochemical or photometric analysis of a blood sample. The integrated measurement system encloses a lancet system, a sensor and a test strip cartridge within a single housing. However, the system described in WO 03/083469 A2 has a number of disadvantages affecting its everyday use. In particular, the system described is a one-piece system in which all the components are integrated in one housing. As a result, the described system takes up a great deal of space and is heavy. Moreover, in the system described, separate tensioning of the integrated lancet system is required. Nor does the system described in WO 03/083469 A2 solve the problem often arising in blood glucose concentration measurements, namely that the properties of the test strips used may vary from batch to batch. This results in sometimes huge variations in the accuracy of the blood glucose concentration measurement. Furthermore, the system described in WO 03/083469 A2 has the disadvantage that an additional test strip cartridge is necessary, test strips. The space taken up by the described system is further increased by this "double housing".

SUMMARY

It is therefore one of the objects of the present invention to make available a system which avoids the described disadvantages of the prior art. In particular, it is aimed to make available a system which is easy to handle, is not susceptible to faults and operating errors, and requires a small amount of space.

A diagnostic system is proposed for determining substance concentrations in liquid samples, in particular for measuring blood glucose in human blood. A magazine system for use in a diagnostic system according to the invention and a method for operating a diagnostic system according to the invention are also proposed. In addition to said use of the diagnostic system according to the invention for measuring blood glucose concentrations, another type of use of the described diagnostic system is also conceivable, for example for rapid and simple analysis of specific samples, for example foodstuffs. Instead of a blood glucose concentration measurement, it is then possible, for example, to perform a measurement of other parameters.

The diagnostic system is intended to have a diagnostic module, and also a lancet system integrated into the diagnostic module. A lancet system can in this case be understood as any desired system for provision of a liquid sample, in particular a needle system for inserting a needle into a sample. In normal cases, this will be a lancet system equipped with a lancet and used to obtain a drop of blood. The lancet can, for example, be exchangeable and can be used once or several times. Such lancet systems can be tensioned in different ways, for example via a linear movement and/or via a rotary movement. However, other lancet systems can also be used by analogy, for example lancet systems or sampling systems for taking samples of foodstuffs.

The diagnostic system also comprises a magazine module which is separate from the diagnostic module and is used to store test strips. These can, for example, involve one of the abovementioned test strips for electrochemical or photometric analysis of liquid samples. In particular, these can be test strips of the above-described kind with a capillary system and one or more electrodes and additional chemical auxiliaries (e.g. enzymes, mediators). By analogy, test strips can also be understood as meaning other test vehicles, in particular small test tubes or continuous rolls of test strips.

The diagnostic system also comprises a connecting device by means of which the magazine module can be connected to the diagnostic module.

The connecting device can have a tensioning device for tensioning the lancet system. Alternatively, the connecting device can also be connected to such a tensioning device of the tensioning the lancet system in such a way that, upon connection of the magazine module to the diagnostic module, the lancet system is tensioned.

Alternatively, or in addition, the connecting device can also have an actuating device for operating the magazine module, in particular for output of at least one test strip, and/or can be connected to such an actuating device. In this alternative of the invention, upon connection of the magazine module to be diagnostic module, at least one test strip is output, where "output" can be understood, for example, as meaning a test strip being pushed forward into a measurement position in which a liquid sample can be received.

Compared to conventional devices known from the prior art, the diagnostic system described has a great many advantages. In particular, the diagnostic module and the magazine module are separate during transport of the described diagnostic system, as long as the diagnostic system is not made ready for use. Therefore, both modules can be stored separately, as a result of which the system is the dismantled state can be packed in a way that takes up little space. Thus, for example, a diabetic does not have to carry both modules about simultaneously, for example in a pocket (e.g. a trouser pocket), and instead can pack the two modules separately and carry then around separately.

The separation of magazine module and diagnostic module also has the effect that, for example by comparison with WO 03/083469 A2, the supply of the diagnostic system with test strips is always safely regulated. No additional, bulky drum of test strips is needed, which would first have to be inserted into the diagnostic system. For refilling with test strips, the entire magazine module can simply be replaced. For example, complete magazine modules can be made commercially available, possibly even in the context of a suitable refund system. A two-wall packaging of the test strips, as is provided for example in WO 03/083469 A2, can be dispensed with.

A further advantage is that the lancet system is tensioned directly upon joining-together of the magazine module and the diagnostic module. A device can also be provided, for example, which annuls the tensioning of the lancet system when the magazine module is separated from the diagnostic module. Overall, therefore, the entire system can be dismantled and then transported in the non-tensioned state, and the lancet system can be automatically tensioned when the two modules are joined together, so that the system is ready for operation immediately after these parts have been joined together.

The system can be extended by providing a data exchange device for exchange of batch information on the test strips between the magazine module and the diagnostic module. As has been described above, this batch information can involve information on how the test strips deviate from a predefined norm, or on how a blood glucose concentration, for example, can be calculated from the measurement information obtained by means of this batch of test strips. This batch information can, for example, involve parameters of a corresponding adaptation function.

In particular, the data exchange device can have a transporter arranged in the magazine module, and a transponder reading unit arranged in the diagnostic module. For example, when the magazine module is connected to the diagnostic module, the transponder arranged in the magazine module can be automatically prompted, by the transponder reading unit arranged in the test strips to the transponder reading unit. These can be commercially available transponders and transponder reading units. This data exchange can, for example, take place automatically as soon as the magazine module is connected to the diagnostic module. This automatic exchange of batch information has the advantage that the probability of errors occurring during transfer of the batch information is drastically reduced.

Alternatively, or in addition, the data exchange device can also have a data memory, in particular an EPROM, arranged in the magazine module. This EPROM is often also designated as "ROM key". This development is useful in combination with a further configuration in which the data exchange device has at least one electrical contact. This electrical contact can, for example, be arranged in the connecting device. In this way, for example, the data memory arranged in the magazine module can be read out directly by means of electrical contacts. This is especially advantageous if wireless data transmission, for example by means of a transponder, is not desired. In many areas of application, wireless data transmissions may be susceptible to interference, for example because interference signals from nearby devices may also be picked up.

The connecting device for connecting the magazine module to the diagnostic module can be configured in different ways. For example, this connecting device can have a push-in device. In a push-in device of this kind, which can have a linear guide for example, the user joins the magazine module and diagnostic module together by effecting a linear displacement of both modules with respect to one another. This linear displacement can in particular be used to tension the lancet system. This is because many lancet systems have one or more linearly acting spring systems which can be subjected to tensioning by means of said linear displacement (see also, for example, U.S. Pat. No. 6,419,661 B1). In particular, the push-in connection can have a dovetail guide. Such a connection between magazine module and diagnostic module is especially stable in mechanical terms.

Moreover, the diagnostic system can be configured in such a way that the tensioning device has a tensioning slide connected to a spring system. This tensioning slide can be arranged, for example, in the diagnostic module. If the connecting device, as above, has a push-in device, for example a dovetail guide, then, when the magazine module and the diagnostic module are joined together by a linear movement, the tensioning slide arranged in the diagnostic module can be caught and displaced linearly relative to the rest of the diagnostic module by a movement of the magazine module, the spring system thus being tensioned. A suitable locking device, for example a simple hook, can then hold the spring system in the tensioned state until the lancet system is triggered, whereupon the hook is freed and the spring system is released and acts on a lancet. Trigger devices of this kind are known from the prior art and will therefore not be described in any more detail here (see also, for example, U.S. Pat. No. 6,419,661 B1).

In addition, the diagnostic module has a computer system and/or a display. The computer system can assume various tasks. In particular, the computer system can be configured in such a way that it records the measurement data, for determination of substance concentrations, either directly or indirectly via corresponding measurement data recording systems and evaluates them accordingly. Various subsystems can be included, for example data memories, in particular volatile and non-volatile memories. The computer system can also have suitable hardware for the recording and exchange of batch information. Thus, for example, a transponder reading unit can be integrated into the computer system. The computer system can, for example, be a microcomputer. Moreover, the computer system can have a device for data output. For example, the computer system can communicate with a display via which visual information can be forward to the person using the diagnostic system, in particular information concerning the blood glucose concentration that has been determined.

The diagnostic system has an actuating device for operating the magazine module, a trigger device for triggering the lancet system, and an operating system for operating the diagnostic module. The actuating device, trigger device and the operating system can form separate operating elements or can also be realized or integrated in a single operating element. The actuating device, the trigger device and the operating system can be provided on the magazine module and/or also on the diagnostic module. It is also conceivable for them to be shared between the diagnostic module and magazine module, for example such that one or more operating elements are provided on the diagnostic module and one or more operating elements are provided on the magazine module.

The diagnostic system can in particular be configured in such a way that it has a vertical grip portion and a substantially horizontal operating surface. In particular, the operating surface can have at least one operating element. Thus, the magazine module in particular can be configured as a grip portion, whereas the diagnostic module has the horizontal operating surface. For example, the diagnostic system made up of the magazine module and diagnostic module can, in the assembled state, have the shape of a T or a pistol shape. This ensures that the diagnostic system is easy to handle. The particular, it is advantageous if the whole diagnostic system can be actuated using one hand. In this case, for example, at least three operating elements can be operated by the fingers of one hand when the magazine module is connected to the diagnostic module. For example, an actuating device for operating the magazine module can be provided in the magazine module and can be operated by the index finger, by the thumb or by the ball of the thumb of a human hand clasping the magazine module. Moreover, a trigger device, for example in the form of a pushbutton, can be provided in the diagnostic module and can, for example, be actuated by the thumb of a hand clasping the magazine module and thus triggers the lancet system. A trigger button that can be actuated by an index finger of a hand clasping the magazine module, is also conceivable. Alternatively, the trigger device can also be configured in such a way that, for example when pressure is extended on a lancet system (for example a spring-mounted lancet cap), the lancet system is automatically triggered by the pressure, with no additional trigger device being necessary. Moreover, one or more pushbuttons can be provided on the diagnostic module and act as an operating system for operating the diagnostic module. These pushbuttons too can, for example, be arranged in such a way that they can be operated by the thumb of a hand clasping the magazine module. This operating system can, for example, reset and initialize the computer system or start up a measurement procedure.

As has been described above, with the diagnostic system according to the invention, it is possible to employ various test strips and also various test methods known to the skilled person, for example electrochemical or photometric test methods. It has proven advantageous to use test strips which, as has been described above, have a capillary system and also a plurality of integrated electrodes. In addition, as has also been described above, the electrodes can be coated with enzymes or mediators, for example, in order to generate free charge carriers in the presence of blood glucose. It has therefore proven advantageous if the magazine module of the diagnostic system has at least one measurement electrode and, when the magazine module is connected to the diagnostic module, the diagnostic module is connectable to at least one test strip via the at least one measurement electrode. Connectable is to be understood as meaning a configuration in which, for example in one position of the test strip, electrodes in the test strip are connected to the at least one measurement electrode.

The magazine system can advantageously be configured in particular as a stack magazine for test strips. However, other configurations are also conceivable, for example roll-type magazines or other systems. The magazine system has an actuating device for output of test strips. This actuating device can, for example, be a lever or a pushbutton, e.g. in the form of a trigger. This actuating device is configured such that it has an actuating button, a push rod and a push element for moving a test strip. The push element can have two pushing edges for a test strip, namely a first pushing edge (measuring edge) and a second edge (ejecting edge). The actuating device can then be configured particularly in such a way that, upon a first actuation of the actuating button, a test strip is taken hold of by the first pushing edge (measuring edge) and is pushed into a measurement position. In this measurement position, the test strip can in particular be contacted from above by the aforementioned measurement electrodes, so that a measurement of a substance concentration, for example a measurement of a blood glucose concentration, can be carried out in this position. The actuating button can then be actuated for example for a second time, whereupon the same test strip is taken hold of by the second pushing edge (ejecting edge) of the push element and is ejected from the magazine module, for example via an output silt. The test strip can then be easily disposed of. Instead of "edges", it is also possible, by analogy, to use other arrangements which have a comparable action, for example suitable grippers, pins, grooves or the like. The described system has in particular the advantage that at no point in the diagnosis does the user have to touch the test strip being contaminated, for example by sweat on the fingers or by dirt on the surface of the hand.

It has also proven advantageous if the magazine module is made substantially airtight or is configured such that dirt and moisture, for example air moisture, are kept well away from the test strips stored in the magazine module. In particular, the magazine module can also contain a desiccant for reducing the air moisture in the magazine module.

For operation with one hand, if the site of puncture by means of a lancet (e.g. a lancet aperture in a lancet cap of the diagnostic system) and the site of application of the liquid sample are closely adjacent. Thus, only a small lateral movement of the diagnostic system is needed to ensure that, after puncturing with the lancet system and production of a drop of blood, the latter is received by the test strip in the measurement position, purpose, the diagnostic system can, for example, be configured such that it has a lancet aperture and a test strip output slit which are advantageously spaced apart from one another by not more than 50 mm, preferably not more than 40 mm, and are especially preferably spaced from one another in a range between 8 mm and 35 mm.

The above-described "T shape" or "pistol shape" of a diagnostic system composed of a magazine module and of a diagnostic module can also be used, according to the invention, without the described automatic tensioning of a lancet system or the automatic output of a test strip upon connection of magazine module and diagnostic module. As has been described above, the diagnostic system can have a substantially vertical grip portion and a substantially horizontal operating surface. In particular, the operating surface can be a surface of the diagnostic module. The distribution of operating elements and the functionality of the individual components of the diagnostic system is distinguished by greatly enhanced above. Compared to known system is distinguished by greatly enhanced ergonomic characteristics and improved handling, and, at the same time, the fact that it can be taken apart means that the bulky "T-shape" of the diagnostic system does not compromise the transport properties.

The invention is described in more detail below on the basis of illustrative embodiments. However, the invention is not limited to the illustrative embodiments shown. The illustrative embodiments are depicted schematically in the figures. Identical reference numbers in the individual figures designate identical elements or elements whose functions are identical or whose functions correspond to one another.

BRIEF DESCRIPTION OF THE DRAWINGS

The following detailed description of the embodiments of the present invention can be best understood when read in conjunction with the following drawings, where like structure is indicated with like reference numerals and in which:

FIG. 3 shows a perspective view of the magazine module according to FIG. 2 with the actuating button pressed in;

FIG. 5 shows a cross-sectional view of the magazine module according to FIG. 4 with the actuating button pressed in;

In order that the invention may be more readily understood, reference is made to the following examples, which are intended to illustrate the invention, but not limit the scope therof.

DETAILED DESCRIPTION

The following description of the preferred embodiment is merely exemplary in nature and is in no way intended to limit the invention or its application or uses.

Figure 1:
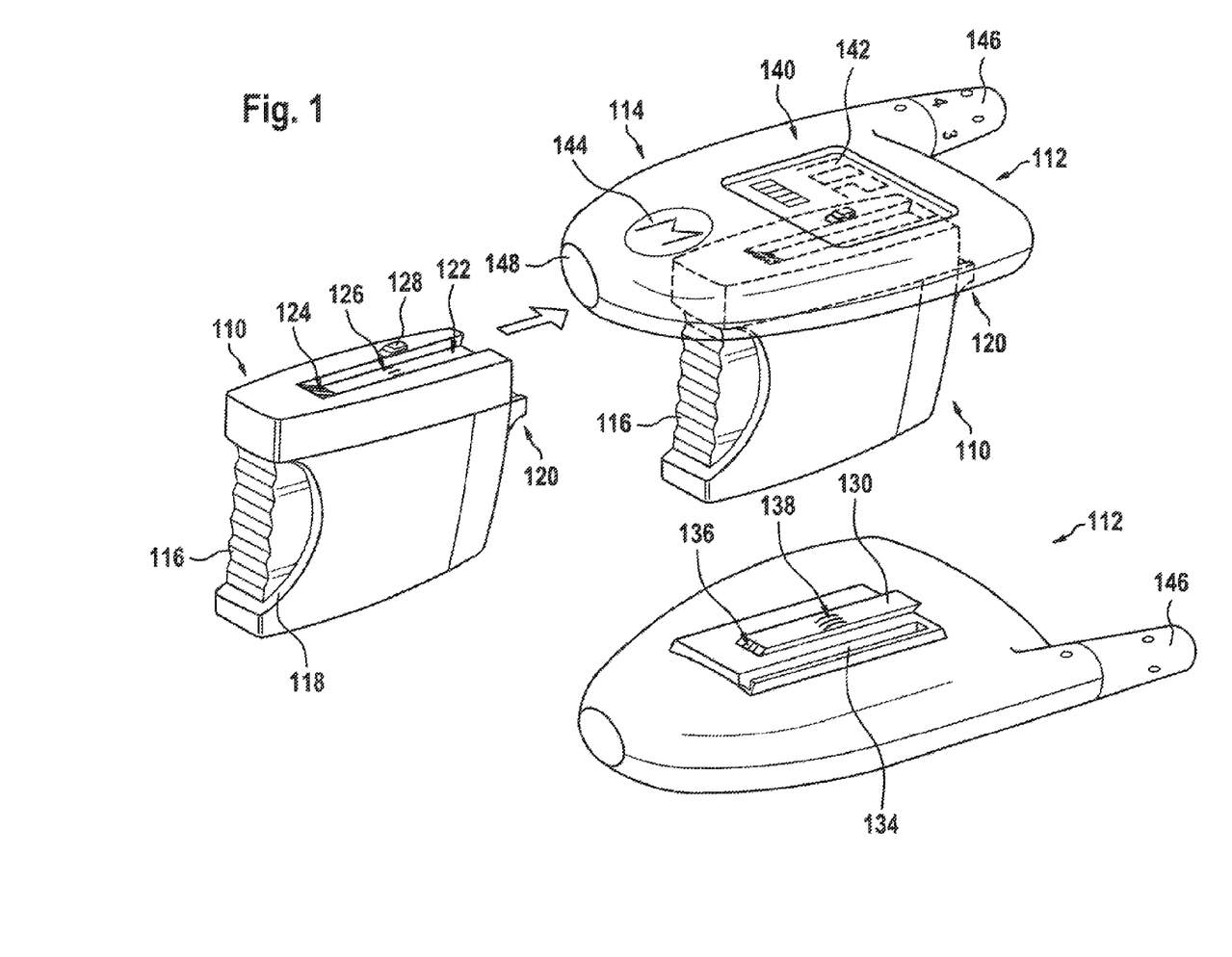
FIG. 1 shows how a magazine module and a diagnostic module are joined together to form a diagnostic system according to the invention.

FIG. 1 is a perspective view showing the assembly of a magazine module 110 and a diagnostic module 112 to form a diagnostic system 114. Here, the diagnostic module is shown from underneath (bottom right of the figure) and from above (in the assembled state in the top right).

The magazine module 110 is designed as a grip portion which, for example, can be clasped in one hand. At one end face, the magazine module 110 has an actuating button 116 as part of an actuating device for outputting test strips from the magazine module (see, for example, reference number 510 in FIG. 5 below). This actuating button 116 is accommodated in a recess 118 in an end face of the magazine module 110. The mode of operation of the actuating button 116 and of the actuating device 510, of which the actuating button 116 forms a part, is described in detail farther below. The surface of the actuating button 116 is ribbed in this illustrative embodiment, in order to improve the hold of the actuating button 116. When the magazine module 110 also has an output unit 120 via which test strips 310 contained in the magazine module 110 (see, for example, FIG. 5 below) can be output and pushed into a test position upon actuation of the actuating device 510, in particular of the actuating button 116.

On its top face, the magazine module 110 has a dovetail-shaped groove 122. This dovetail-shaped groove 122 forms a guide track on the magazine. Two groups of electrical contacts 124, 126 on the magazine are received in the dovetail-shaped groove 122, namely, on the one hand, a group of (in this case three) measurement electrode contacts 124 at the closed end of the dovetail-shaped groove 122 and, on the other hand, a group of (in this illustrative embodiment also three) ROM key contacts 126 for the magazine which arranged which are arranged in the center of the dovetail-shaped groove 122. The function of these contacts 124, 126 is described farther below.

The magazine module 110 also has a driver lug 128 which is arranged alongside the dovetail-shaped groove 122 on the top face of the magazine module 110.

On its underside, the diagnostic module 112 has a dovetail track 130 for the diagnostic module, which dovetail track 130 can be pushed into dovetail-shaped groove 122 on the magazine, a firm connection is thus established between diagnostic module 122 and magazine module 110. The dovetail track 130 on the diagnostic module is mounted on a support plate 132 on the underside of the diagnostic module 112. This support plate 132 has a driver slit 134 into which the driver lug 128 on the top face of the magazine module 110 is able to engage when the diagnostic module 112 is mounted on the magazine module 110.

The dovetail track 130 on the diagnostic module also has two groups of contacts 136, 138. On the one hand, a group of (in this illustrative embodiment three) measurement electrode contacts 136 on an end face of the dovetail track 130 of the diagnostic module and, on the other hand, a group of (in this case also three) ROM key contacts 138 at the center of the dovetail track 130 diagnostic module. The measurement electrode contacts 136 and ROM key contacts 138 of the diagnostic module are arranged in such a way that, when the dovetail track 130 of the diagnostic module come to lie on the measurement electrode contacts 124 of the magazine and the ROM key contacts 138 of the diagnostic module come to lie on the ROM key contacts 126 of the magazine and establish corresponding electrical connections between the magazine module 110 and the diagnostic module 112.

When the diagnostic system 114 is assembled, the diagnostic module 112 also has a substantially horizontal operating surface 140. A display 142, in this illustrative embodiment in particular an LCD display, is set into the operating surface 140. This display 142 can be used to provide the user of the diagnostic system 114 with information, for example the measured results of a blood glucose concentration measurement, and other information too, for example a battery status. Alternatively, the display 142 can also be designed as a touch screen, for example, in which case the diagnostic module 112 or diagnostic system 114 can be operated by touching suitable surface areas on the touch screen.

The operating surface 140 also has an operating button 144 which is set flush into the operating surface 140 and by means of which important functions of the diagnostic system 114 can be operated. For example, this operating button 144 can be used to initialize a computer system (see, for example, reference number 626 in FIGS. 6 and 7 below) contained in the diagnostic module 112 or to start a measurement procedure. The operating button 144 can also be used as an ON and OFF button, although in an alternative to this, or in addition to this, the diagnostic system 114, or the computer system 626 contain therein, can be switched on and off by joining together the magazine module 110 and the diagnostic module 112.

The diagnostic module 112 also has an integrated lancet system (see, or example, reference 612 in FIG. 6 below). This lancet system 612, which is not shown in FIG. 1 because of the perspective representation, has a lancet cap 146 which covers a lancet needle (reference number 628 in FIG. 6 below) held in the lancet cap 146. At its front face, the lancet cap 146 has a lancet aperture 630 (see also FIG. 6) through which the lancet needle 628 can briefly emerge, upon actuation of the lancet system 612, in order to puncture a layer of skin and produce a drop of blood. Drops of blood of less than one microliter are advantageously sufficient here. The lancet cap 146 is at the same time designed as a rotatable setting system in which, by turning the lancet cap 146, it is possible to define how far the lancet needle 628 emerges from the lancet cap 146 or lancet aperture 630 when the lancet system 612 is actuated. In this way, the depth of insertion for obtaining drops of blood can be adjusted in particular, as a result of which the diagnostic system 114 can be adapted to different skin thicknesses, or as a result of which the volume of the drop of blood to be produced is set. The lancet system 612 can be triggered by a trigger button 148 arranged on the end face remote from the front face of the diagnostic module 112.

The diagnostic system 114 shown in FIG. 1 is distinguished by the fact that, on the one hand, it permits a favourable gripping position by clasping the magazine module 110. At the same time, in this gripping position, the observer can easily read information on the display 142 arranged on the operating surface 140 and can operate the diagnostic system 114 using one hand. For transporting the system, the magazine module 110 and the diagnostic module 112 can be easily separated, for example with the diagnostic module 112 being automatically switched off in this way. Separate transport of the two modules 110 and 112 is therefore possible, such that the diagnostic system 114 can be dismantled to save space during transport. To put the diagnostic system 114 into operation, the use of both hands is initially required, the diagnostic module 112 being inserted with its dovetail track 130 into the dovetail-shaped groove 122 on the magazine. In doing this, the diagnostic system 114 is for example automatically started, that is to say, for example, in particular a computer system 626 contained in the diagnostic system 114 is initialized. At the same time, joining the two modules 110, 112 together has the effect that the lancet system 612 contained in the diagnostic module 112 is tensioned. Moreover, when the two modules 110, 112 are joined together, an electrical contact is established between the diagnostic module 112 and the magazine module 110, as a result of which, on the one hand, measurement electrodes (see, for example, reference number 422 in FIG. 4 below) arranged in the magazine module 110 can be read out from the diagnostic module 112, and, as a result of which, on the other hand, batch information concerning the test strips 310 contained in the magazine module 110 can be automatically transferred to the diagnostic module 112 via the ROM key contacts 126, 138. The source of error arising when the user enters incorrect batch information into the diagnostic system 114 and the source of error arising when there is interference in a wireless transmission of batch information are thereby avoided (see above).

Figure 2:
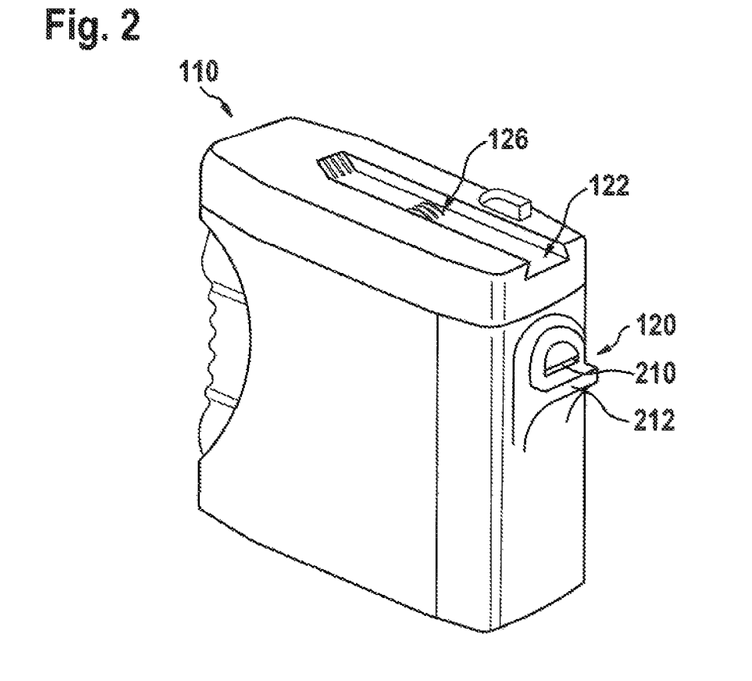
FIG. 2 shows a perspective view of a magazine module.
Figure 3:
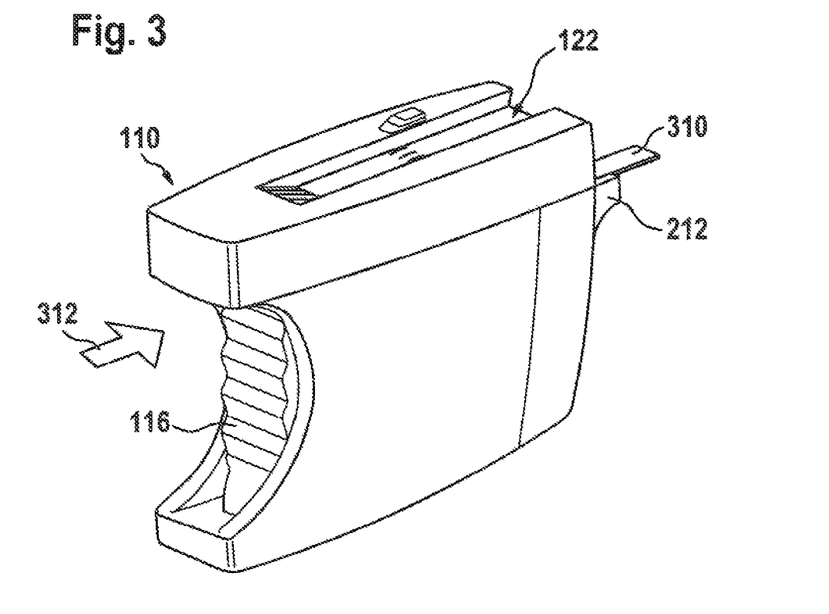

The magazine module 110 is once again shown in different perspective views in FIGS. 2 and 3. FIG. 2 is a front view in which the output unit 120 is shown in detail. An important element of the output unit 120 is an output slit 210 which is arranged horizontally and has approximately the width and thickness of a test strip 310. The output slit 210 can additionally be closed by a sealing lip (see, for example, reference number 526 in FIG. 4), for example a rubber sealing lip, which allows a test strip 310 to be pushed out from from the output slit 210 but substantially prevents introduction of moisture and dirt into the interior of the magazine module 110. Moreover, the output unit 210 has a retaining lip 212 which supports a test strip 310 in the measurement position (see FIG. 3), such that part of this test strip 310 extends into the magazine module 110 and is there in contact with measurement electrodes and part of it extends out of the magazine module 110 in order to receive a drop of blood there, for example.

In FIG. 3, the magazine module 110 is shown in the measurement position with the actuating button 116 pressed in, the direction of actuation of the actuating button 116 being symbolized by the arrow 312. In this example, as will be explained farther below, the actuating button 116 has a dual function. A single actuation of the actuating button 116 in the direction of actuation 312 has the effect that a test strip 310 is pushed partly out of the magazine module 110 through the output slit 210 and is thus positioned in a measurement position (see above). In this position, the protruding end of the test strip 310 can receive drops of blood which are transported by a capillary system into the part of the test strip 310 lying inside the magazine module 110, to a corresponding electrode system. This electrode system, which, as is described above, is coated for example with enzymes and mediators, is in contact with measurement electrodes (see reference number 422 in FIG. 4 below) in the inside of the magazine module 110, and these in turn can be read out via a measurement electrode line system (see reference number 420 in FIG. 4) and the measurement has been completed, renewed actuation of the actuating button 116 in the direction of actuation 312 has the effect, finally, that the used test strip 310 is completely ejected from the magazine module 110, so that it can be discarded.

Figure 4:
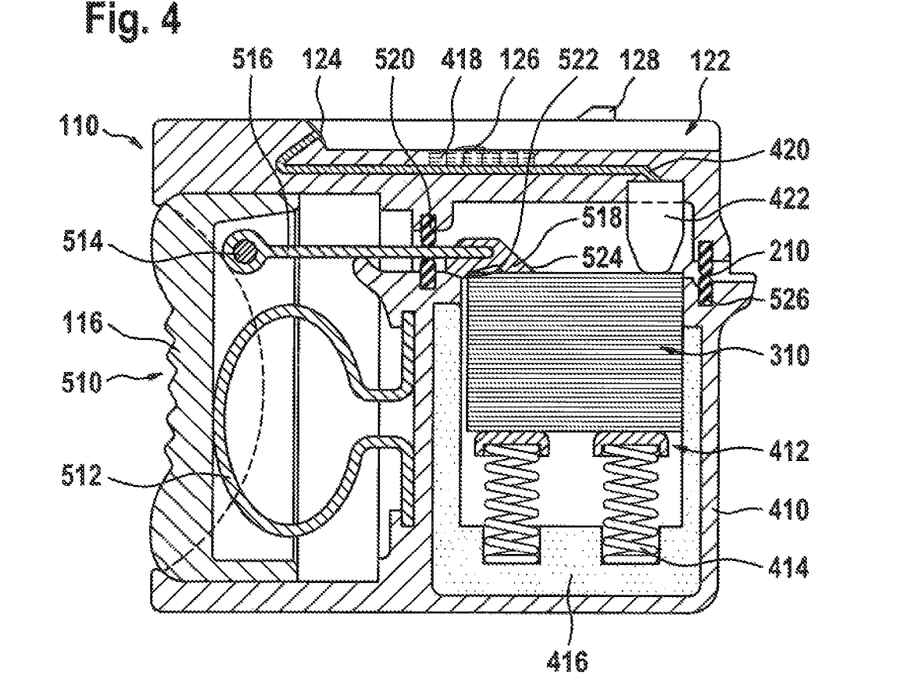
FIG. 4 shows a cross-sectional view of a magazine module according to FIG. 2.
Figure 5:
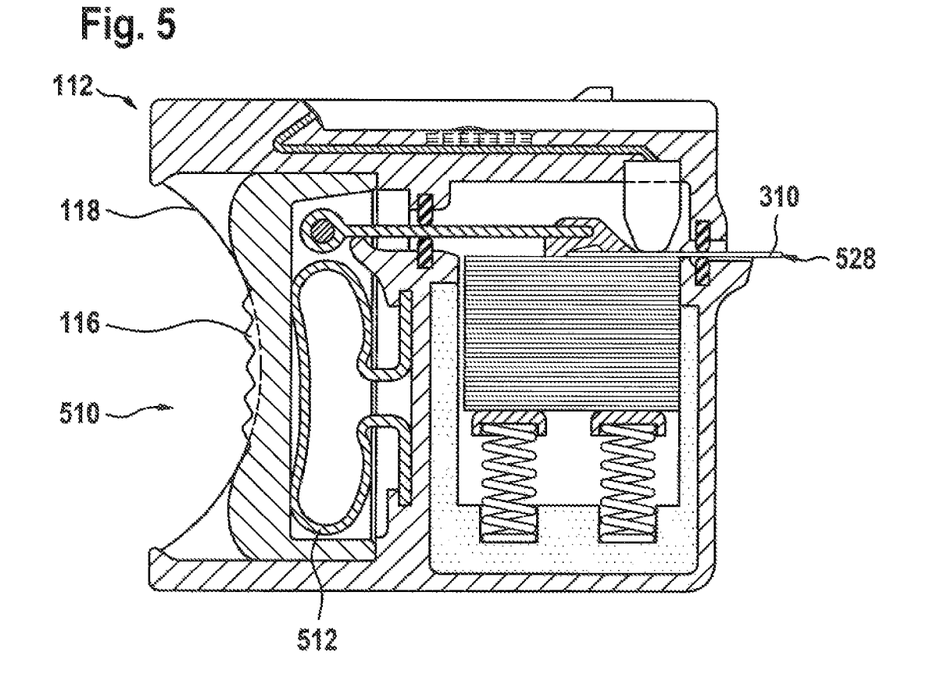

A cross-sectional view of the magazine module 110 is shown in FIGS. 4 and 5, the cross-sectional view according to FIG. 4 corresponding to the perspective view according to FIG. 2, and the cross-sectional view according to FIG. 5 corresponding to the perspective view according to FIG. 3 with actuating button 116 pressed in the direction of actuation 312. The magazine module 110 has a housing 410 into which a stack magazine 412 for test strips 310 is formed. In this stack magazine 412, the test strips 310 lie horizontally one above the other and are pressed upwards by a spring system 414. In the stack magazine 412, the test strips 310 are additionally surrounded by a desiccant 416, for example silica gel, which reduces the air moisture inside the stack magazine 412.

The dovetail-shaped groove 122 and the driver lug 128 can also once again be seen in the views according to FIGS. 4 and 5. The arrangement of the measurement electrode contacts 124 on the magazine and of the ROM key concepts 126 on the magazine can also be seen. The ROM key contacts 126 are in direct communication with a data memory 418 (ROM key) which contains batch information concerning the test strips 310. This batch information can be read out from the diagnostic module 112 via the ROM key contacts 126. The measurement electrode contacts 124 on the magazine communicate, via a measurement electrode line system 420, with measurement electrodes 422 arranged above the stack magazine 412. When a test strip 310, so that these electrodes on the test strip 310 can be read out, via the measurement electrode contacts 124 on the magazine and the measurement electrode contacts 136 on the diagnostic module, from said diagnostic module 112 and can be evaluated there in a computer system 626.

The magazine module 110 also has an actuating device 510 whose mode of operation will be described through a comparison of FIGS. 4 and 5. As has already been described above, the actuating device 510 has an actuating button 116 which can be pressed in the direction of actuation 312 (see FIG. 3), for example by thumb or by the ball of the thumb. The actuating device 510 also has a spring mechanism 512 which exerts a force on the actuating button 116 counter to the direction of actuation 312 (see FIG. 3). In this illustrative embodiment, the spring mechanism 512 is made of flexible material, for example a plastic, and has, for example, the shape of the Greek letter omega. The actuating device 510 also has a push rod 516 which is mounted pivotably on the actuating button 116 via an axle 514 and which, at its end remote from the axle 514, is connected to a push element 518. The push rod 516 protrudes into the stack magazine 412 in such a way that the axle 514 is arranged outside the stack magazine and the push element 518 is arranged inside the stack magazine 412. The site of entry of the push rod 516 into the stack magazine 412 is sealed off by a first sealing lip 520 in order to reduce or minimize penetration of moisture into the stack magazine 412.

The push element 518, which is mounted at the end of the push rod 516 remote from the axle 514 and is easily pivotable about the push rod 516, has two pushing edges 522, 524. A first pushing edge 522, also called the measuring edge, which is arranged closer to the axle 514, and a second pushing edge 524, also called the ejecting edge, which is arranged farther away from the axle 514. The function of these two pushing edges 522, 524 is clear from a comparison of FIGS. 4 and 5. Upon a first actuation of the actuating button 116, the spring mechanism 512 is compressed and the push rod 516 is pushed through the first sealing lip 520 and farther into the stack magazine 412, and the first test strip 310, at its end towards the axle 514, is taken hold of by the first pushing edge 522 and is pushed partially out through the output slit 210 provided with a second sealing lip 526. When the actuating button 116 is pressed in fully, as is shown in FIG. 5, the test strip 310 is located in a measurement position. As has been described above, a drop of blood can be received via the tip 528 of the test strip 310, which drop of blood is then conveyed via a capillary system in the interior of the test strip 310 to an electrode system which is arranged underneath the measurement electrodes 422 in the measurement position shown in FIG. 5 and which is made contact with by the measurement electrodes 422 (see above).

Then, if no further force is exerted on the actuating button 116, the actuating button 116 moves back again to its starting position shown in FIG. 4, driven by the force of the spring mechanism 512. The push rod 516 and thus also the push element 518 are also moved back to the position shown in FIG. 4. However, the uppermost test strip 310 remains in the measurement position shown in FIG. 5. The measurement electrodes 422 act as a counterpart to the spring system 414 and prevent further test strips 310 from being able to move up from below. If the actuating button 116 is then moved again in the direction of actuation 312, the push rod 516, with the push element 518 mounted pivotably thereon, is pushed once again into the stack magazine 412. The push element 518 is preferably mounted pivotably about the second pushing edge 524. Accordingly, upon this second insertion of the push rod 516 into the stack magazine 412, the second pushing edge 524 takes hold of that end of the uppermost test strip 310 situated closer to the axle 514. Since this second pushing edge 524 is situated farther from the axle 514 than is the first pushing edge 522, this second insertion of the push element 518 means that the test strip 310 is pushed father out of the output slit 210, so that finally it completely leaves the out put slit 210 or is pushed out to such an extent that, because most of its weight is now situated outside the magazine module 110, it is ejected completely from the output slit 210 by its gravitational force. Alternatively, or in addition, the push element 518 can also push the measurement electrodes 422 upwards upon its insertion into the stack magazine 412, so that the push element 518 can be brought closer to the output slit 210. Overall, the mechanism illustrated here thus provides a system in which, upon a first actuation of the actuating device 510, a test strip 310 is initially pushed into a measurement position and then, upon a second actuation of the actuating device 510, the same test strip 310, which has now been used, is ejected.

Figure 6:
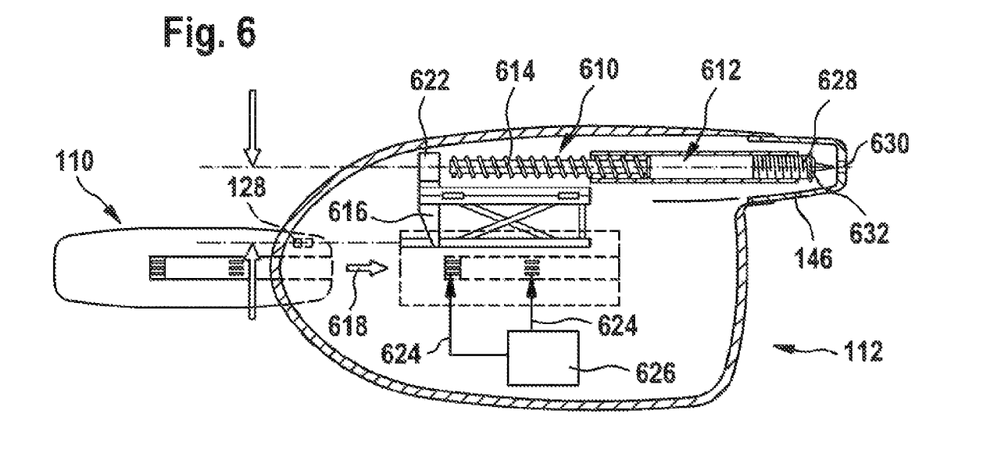
FIG. 6 shows a cross-sectional view of a diagnostic module before attachment of a magazine module.
Figure 7:
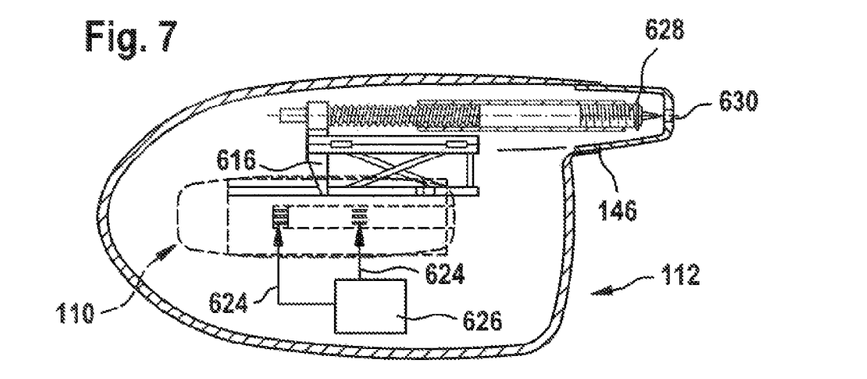
FIG. 7 shows a cross-sectional view of the arrangement according to FIG. 6 after attachment of the magazine module.
Figure 8:
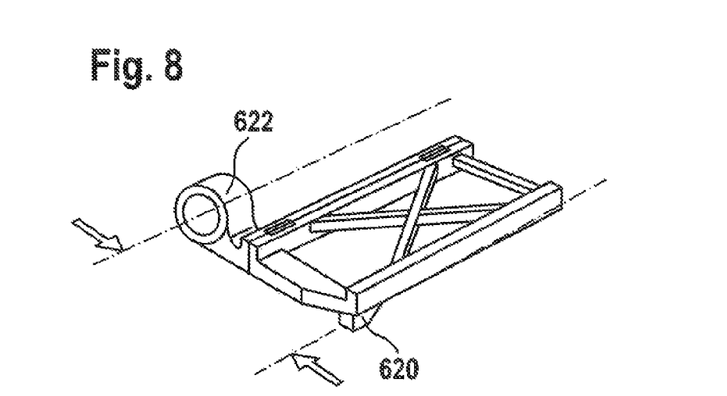
FIG. 8 shows a perspective view of a tensioning slide for a lancet system.
Figure 9A:
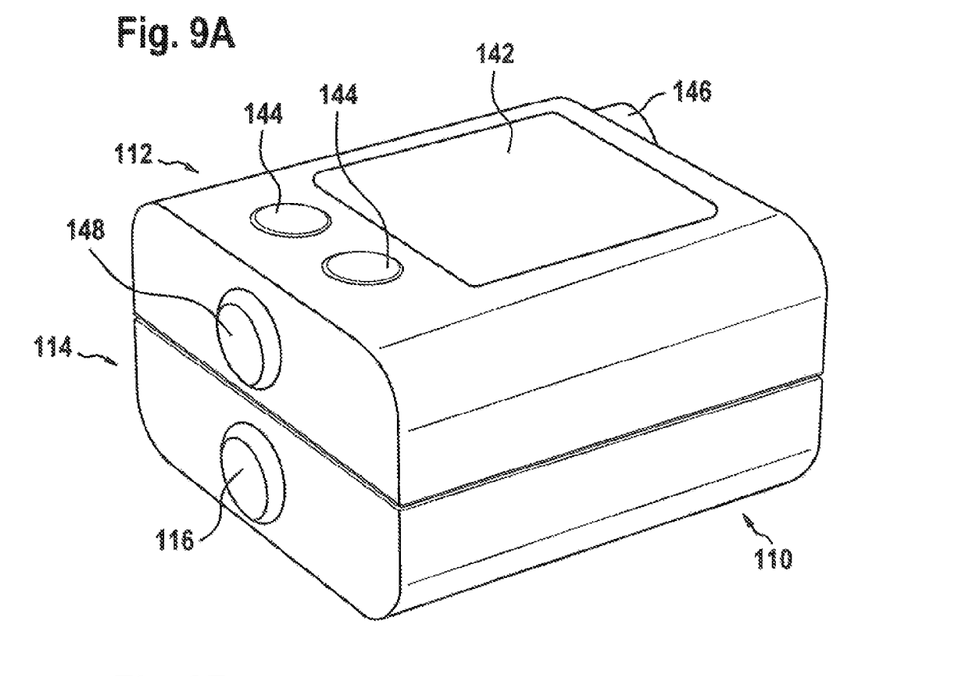
FIG. 9A shows a perspective view, from the rear, of a diagnostic system in stack form, as an alternative to FIG. 1.
Figure 9B:
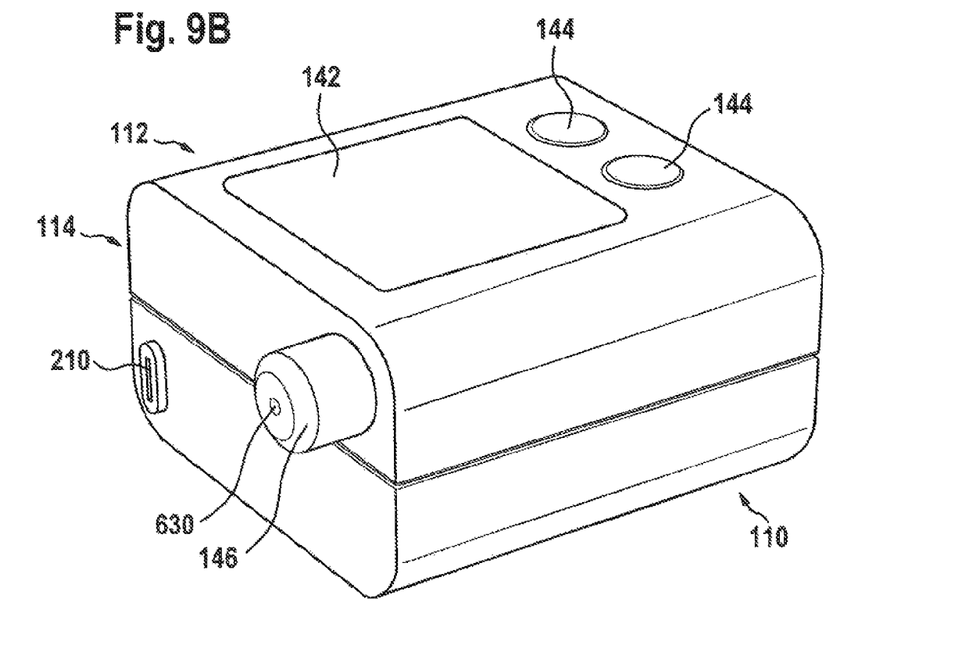
FIG. 9B shows a perspective view of the diagnostic system according to FIG. 9A from the front.

A cross-sectional and greatly simplified view of a diagnostic module 112 is shown in FIGS. 6 and 7. These show particularly clearly how a tensioning device 610 arranged in diagnostic module 112 for tensioning a lancet system 612 is tensioned upon connection of a magazine module 110 to the diagnostic module 112. The tensioning device 610 has a helical spring 614, and also a tensioning slide 616. The tensioning slide 616 is shown also in a perspective view in FIG. 8. When the magazine module 110 is connected in direction of insertion 618 to the diagnostic module 112 by means of the above-described push-in connection comprising the dovetail-shaped groove 122 on the magazine module 110 and the dovetail track 130 on the diagnostic module, the driver lug 128 on the top face of the magazine module 110 now protrudes through the driver slit 134 in the support plate 132 into the diagnostic module 112 and can there engage a tensioning lug 620 of the tensioning slide 616 also protruding into the driver slit 134. The tensioning slide 616 is pushed in the direction of insertion 618. The tensioning slide 616 is connected by a spring bearing 622 to the helical spring 614 of the lancet system 612. When the tensioning slide 616 moves in the direction of insertion 618, the helical spring 614 of the lancet system 612 is compressed likewise in the direction of insertion 618. In this way, the lancet system 612 is tensioned (see FIG. 7, tensioned position). When the magazine module 110 and diagnostic module 112 are completely connected to one another, the measurement electrode contacts 124 on the magazine also come into contact with the measurement electrode contacts 136 on the diagnostic module, as can be seen in FIG. 7, and the ROM key contacts 126 on the magazine come into contact with the ROM key contacts 138 on the diagnostic module. These contacts 124, 136, 126, 138 can thus be read out via measurement lines 624 from a computer system 626 arranged in diagnostic module 112. In this way, the computer system 626 receives both said batch information concerning the test strips 310 and also the actual blood glucose concentration measurement signals delivered by the measurement electrodes 422.

The lancet system 612 comprises an exchangeable lancet needle 628. If, in the tensioned state of the lancet system 612 shown in FIG. 7, the trigger button 148 (not shown here; see FIG. 1) is actuated, the hitherto blocked lancet needle 628 is released (for example by release of a corresponding locking hook), and the tensioned helical spring 614 acts on the lancet needle 628 and drives it abruptly through a lancet aperture 630 in the lancet cap 146. This penetrating movement of the lancet needle 628 is braked by a limit stop 632 which abuts on the edges of the lancet aperture 630 and thus defines a maximum depth of emergence of the lancet needle 628 from the lancet aperture 630. By changing the position of the lancet cap 146 relative to the rest of the diagnostic module 112 (for example by means of a rotational movement and a thread via which the lancet cap 146 is connected to the rest of the diagnostic module 112), a depth of penetration of the lancet system 612 can thus be set.

FIGS. 9A and 9B and FIGS. 10A and 10B show perspective views of two further embodiments of diagnostic system 114 according to the invention which represent alternatives to the first embodiment shown in FIGS. 1 to 8. Here, FIGS. 9A and 10A each show a view from the rear, and FIGS. 9B to 10B each show a view from the front, that is to say looking at the face on which the lancet cap 146 is arranged.

The function of the elements, in particular of the operating elements 144, the actuating button 116 and the trigger button 148, is identical or functionally similar to the first illustrative embodiment set out above. The structure of the diagnostic module 112 and of the magazine module 110 can, in principle, also be identical or similar to the structure described above.

The main difference between, on the one hand, the illustrative embodiments according to FIGS. 9A, 9B, 10A and 10B and, on the other hand, the above first illustrative embodiments lies, however, in the geometry of the arrangement of magazine module 110 and diagnostic module 112 relative to one another and in the way they are assembled to give the finished diagnostic system 114. Whereas the preferred first illustrative embodiment set out above has substantially the shape of a T (also called a "pistol" arrangement), the second illustrative embodiment shown in FIGS. 9A and 9B has, in the assembled state of the diagnostic system 114, a "stack shape", with a geometry substantially corresponding to a cuboid with a square base surface of ca. 50 mm×50 mm and a height of ca. 30 mm. Approximately half of this cuboid is formed by the magazine module 110 (which thus has the shape of a right parallelepiped with a height of ca. 15 mm) and the other half is formed by the diagnostic module 112. The stack shape according to FIGS. 9A and 9B also saves a lot of space in the assembled state of the diagnostic system 114. Dimensions other than those specified are also possible, in particular also unequal dimensions of magazine module 110 and diagnostic module 112.

Figure 10A:
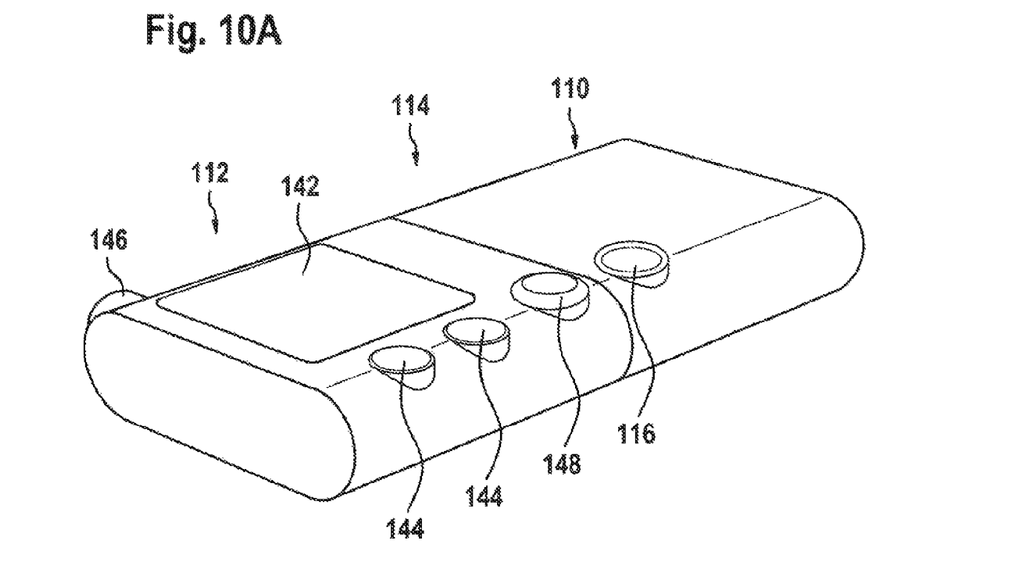
FIG. 10A shows a perspective view, from the rear, of a diagnostic system in serial form, as an alternative to FIG. 1 and FIGS. 9A and 9B.
Figure 10B:
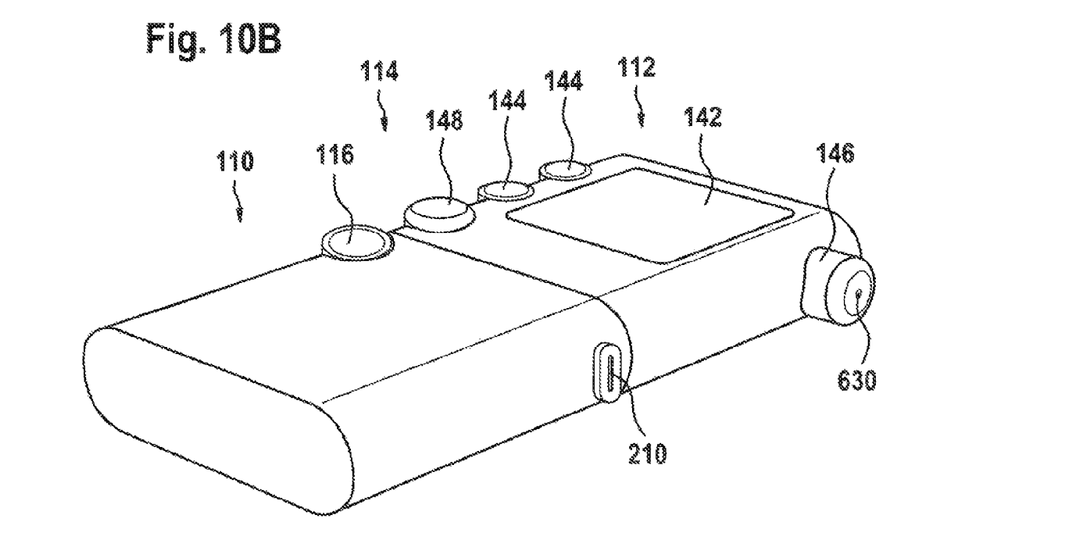
FIG. 10B shows a perspective view of the diagnostic system according to FIG. 10A from the front.

Corresponding, FIGS. 10A and 10B show a third alternative design. Here, the magazine module 110 and diagnostic module 112, analogously to FIGS. 9A and 9B, again have a cuboid shape (edge lengths again 50 mm×50 mm×15 mm). However, in this illustrative embodiment, both modules 110, 112 are joined together at their end faces, so that a "row shape" is obtained, that is to say a cuboid with an edge length of ca. 100 mm×50 mm×15 mm. This shape is particularly easy to grip, while at the same time, however, the display is still easily readable and, in the assembled state, less space is taken up. Dimensions other than those specified are also possible, in particular also unequal dimensions of magazine module 110 and diagnostic module 112.

In the illustrative embodiments according to FIGS. 9A, 9B, 10A and 10B, both modules 110 and 112 can be connected to one another analogously to the connection shown in FIG. 1, for example via a dovetail-shaped groove 122 and dovetail track 130 on the diagnostic module (groove 122 and track 130 can of course also be provided the other way around). The tensioning of the lancet system 612 and the exchange of data and signals can also be effected analogously to the illustrative embodiment according to FIG. 1.

Figure 11:
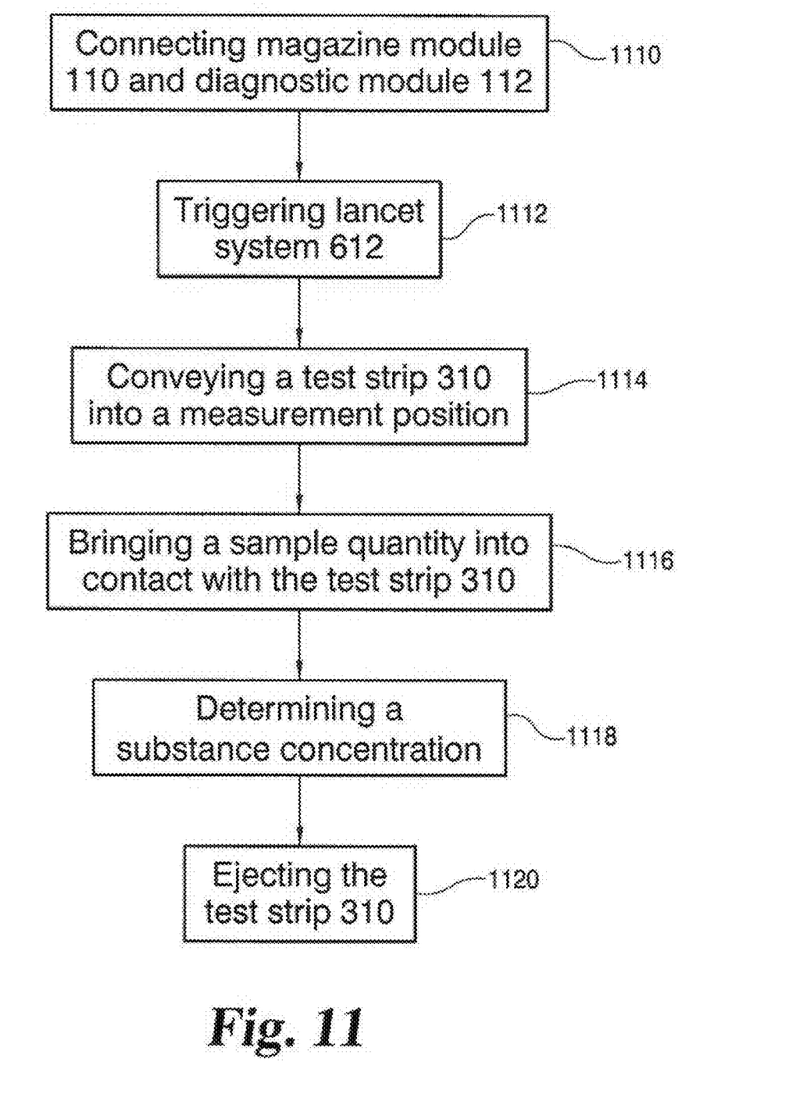
FIG. 11 shows a sequence of an example of a method according to the invention for operating a diagnostic system according to the invention.

FIG. 11, finally, shows a schematic sequence of a possible set-up of a method according to the invention for operating a diagnostic system 114 according to the invention. The method steps shown do not necessarily have to be performed in the illustrated sequence. Other method steps not shown here can also be performed.

First, in the method step 1110, a magazine module 110 with test strips 310, for example according to the illustrative embodiment in FIG. 1, is connected to a diagnostic module 112, a lancet system 612 thus being tensioned. Then, in method step 1112, the lancet system 612, is triggered, for example by actuation of a trigger button 148, as a result of which a quantity of liquid sample, in particular a drop of blood, is made ready.

In method step 1114, a test strip 310 is then conveyed from the magazine module 110 into a measurement position, for example by actuation of an actuating device 510 according to FIGS. 4 and 5. Then, in method step 1116, the sample is brought into contact with the test strip 310. Then, in step 1118, the substance concentration of at least one defined substance, for example glucose, in the sample is determined, for example on the basis of the above-described method of current-voltage measurement. Then, in optional method step 1120, the test strip 310 just used can be ejected, for example, as has been described above, by means of renewed actuation of the actuating device 510.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A diagnostic system for determining substance concentrations in liquid samples, the system comprising:
   a diagnostic module with a lancet system integrated into the diagnostic module;
   a magazine module which is separate from the diagnostic module and is used to store test strips; and
   a connecting device for mechanically connecting and disconnecting the magazine module to the diagnostic module, wherein the connecting device has or is connected to a tensioning device and wherein the tensioning device is adapted for tensioning the lancet system upon connection of the magazine module to the diagnostic module.

2. The system of claim 1, wherein the tensioning device has a tensioning slide connected to a spring system.

3. A diagnostic system for determining substance concentrations in liquid samples, the system comprising:
   a diagnostic module with a lancet system integrated into the diagnostic module;
   a magazine module which is separate from the diagnostic module and is used to store test strips; and
   a connecting device for mechanically connecting the magazine module to the diagnostic module, wherein the connecting device has or is connected to an actuating device for operating the magazine module such that upon connection of the magazine module to the diagnostic module, at least one test strip is output.

4. The system of claim 1, further comprising a data exchange device for exchange of batch information on the test strips between the magazine module and the diagnostic module.

5. The system of claim 4, wherein the data exchange device has a transponder arranged in the magazine module, and a transponder reading unit arranged in the diagnostic module.

6. The system of claim 4, wherein the data exchange device has a data memory arranged in the magazine module.

7. The system of claim 4, wherein the data exchange device has at least one electrical contact arranged in the connecting device.

8. The system of claim 1, wherein the connecting device has a push-in connection.

9. The system of claim 8, wherein the push-in connection has a dovetail guide.

10. The system of claim 1, wherein the diagnostic module has a display and/or a computer system.

11. A diagnostic system for determining substance concentrations in liquid samples, the system comprising:
   a diagnostic module with a lancet system integrated into the diagnostic module;
   a magazine module which is separate from the diagnostic module and is used to store test strips;
   a connecting device for mechanically and electrically connecting the magazine module to the diagnostic module; and
   a data exchange device for exchange of batch information on the test strips between the magazine module and the diagnostic module,
   wherein the diagnostic module has or is connected to a display for displaying the substance concentration determined by the diagnostic module, and
   wherein the connecting device has or is connected to a tensioning device for tensioning the lancet system such that upon connection of the magazine module to the diagnostic module, the lancet system is tensioned.

12. The system of claim 11, wherein the tensioning device has a tensioning slide connected to a spring system.

13. A diagnostic system for determining substance concentrations in liquid samples, the system comprising:
   a diagnostic module with a lancet system integrated into the diagnostic module;
   a magazine module which is separate from the diagnostic module and is used to store test strips;
   a connecting device for mechanically and electrically connecting the magazine module to the diagnostic module; and
   a data exchange device for exchange of batch information on the test strips between the magazine module and the diagnostic module;
   wherein the diagnostic module has or is connected to a display for displaying the substance concentration determined by the diagnostic module, and
   wherein the connecting device has or is connected to an actuating device for operating the magazine module such that upon connection of the magazine module to the diagnostic module, at least one test strip is output.

14. The system of claim 11, wherein the data exchange device has a transponder arranged in the magazine module, and a transponder reading unit arranged in the diagnostic module.

15. The system of claim 11, wherein the data exchange device has a data memory arranged in the magazine module.

16. The system of claim 11, wherein the data exchange device has at least one electrical contact arranged in the connecting device.

17. The system of claim 11, wherein the connecting device has a push-in connection.

18. The system of claim 17, wherein the push-in connection has a dovetail guide.

19. A diagnostic system for determining substance concentrations in liquid samples, the system comprising:
   a diagnostic module with a lancet system integrated into the diagnostic module; and
   a magazine module which is separate from the diagnostic module and is used to store test strips,
   wherein the diagnostic system comprises the following operating elements:
     an actuating device for operating the magazine module;
     a trigger device for triggering the lancet system; and
     an operating system for operating the diagnostic module, and
   wherein the diagnostic system has a vertical grip portion and a horizontal operating surface, wherein the operating surface is perpendicular to the grip portion and wherein the operating surface comprises a display.

20. The system of claim 19, wherein the operating surface has at least one operating element.

21. The system of claim 19, wherein the magazine module has at least one measurement electrode and, when the magazine module is connected to the diagnostic module, the diagnostic module is connectable to at least one test strip via the at least one measurement electrode.

22. The system of claim 19, wherein the magazine module has a stack magazine for the test strips.

23. The system of claim 19, wherein the actuating device is adapted for use in outputting the test strips.

24. The system of claim 23, wherein the actuating device comprises: an actuating button, a push rod and a push element for moving a test strip, the push element having at least a first pushing edge and a second pushing edge for holding a test strip.

25. A diagnostic system for determining substance concentrations in liquid samples, the system comprising:
- a diagnostic module with a lancet system integrated into the diagnostic module;
- a magazine module which is separate from the diagnostic module and is used to store test strips; and
- a connecting device for mechanically connecting and disconnecting the magazine module to the diagnostic module;
- wherein the system has a vertical grip portion and a horizontal operating surface, wherein the operating surface is perpendicular to the grip portion and wherein the operating surface comprises a display.

26. The system of claim 1 wherein the connecting device is adapted for electrically connecting and disconnecting the magazine module to the diagnostic module.

27. The system of claim 26 wherein the connecting device is adapted for directly electrically connecting and disconnecting the magazine module to the diagnostic module.

28. The system of claim 3 wherein the connecting device is adapted for electrically connecting and disconnecting the magazine module to the diagnostic module.

29. The system of claim 28 wherein the connecting device is adapted for directly electrically connecting and disconnecting the magazine module to the diagnostic module.

30. The system of claim 3, further comprising a data exchange device for exchange of batch information on the test strips between the magazine module and the diagnostic module.

31. The system of claim 30, wherein the data exchange device has a transponder arranged in the magazine module, and a transponder reading unit arranged in the diagnostic module.

32. The system of claim 30, wherein the data exchange device has a data memory arranged in the magazine module.

33. The system of claim 30, wherein the data exchange device has at least one electrical contact arranged in the connecting device.

34. The system of claim 3, wherein the connecting device has a push-in connection.

35. The system of claim 34, wherein the push-in connection has a dovetail guide.

36. The system of claim 3, wherein the diagnostic module has a display and/or a computer system.

* * * * *